(12) United States Patent
Xu et al.

(10) Patent No.: US 9,714,256 B2
(45) Date of Patent: Jul. 25, 2017

(54) BLUE ELECTROCHROMIC COMPOUND, PREPARATION METHOD AND SUBASSEMBLY THEREOF

(71) Applicants: BOE TECHNOLOGY GROUP CO., LTD., Beijing (CN); UNIVERSITY OF SCIENCE AND TECHNOLOGY OF CHINA, Hefei, Anhui (CN)

(72) Inventors: Chunye Xu, Beijing (CN); Sai Mi, Beijing (CN); Jianming Zheng, Beijing (CN)

(73) Assignees: BOE TECHNOLOGY GROUP CO., LTD., Beijing (CN); UNIVERSITY OF SCIENCE AND TECHNOLOGY OF CHINA, Hefei, Anhui (CN)

( * ) Notice: Subject to any disclaimer, the term of this patent is extended or adjusted under 35 U.S.C. 154(b) by 0 days.

(21) Appl. No.: 14/651,005

(22) PCT Filed: Nov. 7, 2014

(86) PCT No.: PCT/CN2014/090577
§ 371 (c)(1),
(2) Date: Jun. 10, 2015

(87) PCT Pub. No.: WO2015/090124
PCT Pub. Date: Jun. 25, 2015

(65) Prior Publication Data
US 2016/0264595 A1  Sep. 15, 2016

(30) Foreign Application Priority Data
Dec. 17, 2013 (CN) .......................... 2013 1 0695498

(51) Int. Cl.
*C07D 495/04* (2006.01)
*C09K 9/02* (2006.01)

(52) U.S. Cl.
CPC .............. *C07D 495/04* (2013.01); *C09K 9/02* (2013.01); *C09K 2211/1007* (2013.01); *C09K 2211/1088* (2013.01); *C09K 2211/1092* (2013.01); *C09K 2211/1096* (2013.01)

(58) Field of Classification Search
CPC  C07D 495/04; C09K 9/02; C09K 2211/1088; C09K 2211/1092; C09K 2211/1096; C09K 2211/1007
See application file for complete search history.

(56) References Cited

U.S. PATENT DOCUMENTS 8,890,130 B2 * 11/2014 Sotzing ............... H01L 51/0034
257/40
2011/0233532 A1   9/2011 Sotzing et al.
2013/0150552 A1   6/2013 Amb et al.
2013/0165614 A1   6/2013 Amb et al.

FOREIGN PATENT DOCUMENTS

| CN | 102482569 A | 5/2012 |
| CN | 102870040 A | 1/2013 |
| CN | 103328604 A | 9/2013 |
| CN | 103666445 A | 3/2014 |
| WO | 2009087364 A1 | 7/2009 |

OTHER PUBLICATIONS

Sinness, CA143:193677, abstract only of Materials Research Society Symposium Proceedings, 2005, 846(Organic and Nanocomposite Optical Materials), 121-126.*
Hammond, CA 156:337666, abstract only of J of Materials CHemistry, 2012, vol. 22(14), 6752-6764.*
International Search Report Appln. No. PCT/CN2014/090577; Dated Feb. 3, 2015.
Written Opinion of the International Searching Authority Appln. No. PCT/CN2014/090577; Dated.
First Chinese Office Action issued Sep. 2, 2014; Appln. No. 201310695498.3.
Notification to Grant Patent Right issued Jan. 13, 2015; Appln. No. 201310695498.3.

* cited by examiner

*Primary Examiner* — D M Seaman
(74) *Attorney, Agent, or Firm* — Ladas & Parry LLP

(57) ABSTRACT

One class of blue thiophene electrochromic compounds include 3,4-(2,2-bis(2-oxo-3-phenylpropyl))propylenedioxythiophene, 3,4-(2,2-bis(2-oxo-3-phenylbutyl))propylenedioxythiophene, and 3,4-(2,2-bis(2-oxo-3-phenylamyl))propylenedioxythiophene. The thiophene electrochromic compounds can change color between blue and transparency. The thiophene compounds can be electropolymerized on the surface of the ITO glass to form a film. The film has characteristics of low driving voltage (within ±1V), fast response time, and large transmittance difference between colored-state and bleached-state (up to 77.5%). The thiophene electrochromic compounds can be used in the electrochromic window, rearview mirror, electrochomeric display, and the like.

2 Claims, 6 Drawing Sheets

BLUE ELECTROCHROMIC COMPOUND, PREPARATION METHOD AND SUBASSEMBLY THEREOF

FIELD OF INVENTION

Embodiments of the present invention relate to a blue electrochromic compound, preparation method and subassembly thereof.

BACKGROUND

Electrochromic materials have been one of focuses in material science researches in recent years. Compared to inorganic or organic small molecule electrochromic materials, polymer electrochromic materials have advantages of better coloring efficiency; fast electrochromic response; good chemical stability; easy preparation; longer cycle life; color-memory function; and adjustable color shade, Bayer company in German firstly synthesized a derivative of polythiophene, poly(ethylenedioxythiophene) (PEDOT), which is a thiophene electrochromic polymer whose color can change between blue and transparent. After that, a series of blue polythiophene electrochromic polymers has been developed. However, existing blue polythiophene electrochromic materials generally have poor transmittance, and no method for preparing blue polythiophene electrochromic materials on a large scale has been developed, which limits the spreading and application of such materials.

The present invention aims to provide a novel blue thiophene electrochromic compound having high transmittance and preparation method thereof.

SUMMARY

An embodiment of the present invention provides a blue thiophene electrochromic compound as shown by formula (I),

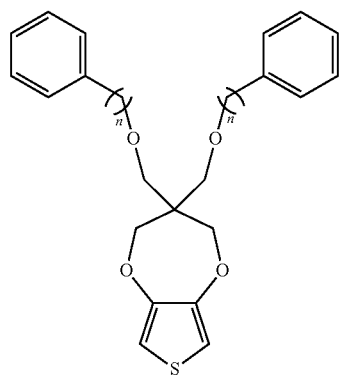

(I)

wherein, n is 1, 2, or 3.

In an embodiment of the present invention, said compound is 3,4-(2,2-bis(2-oxo-3-phenylpropyl))propylenedioxythiophene as shown by formula (II),

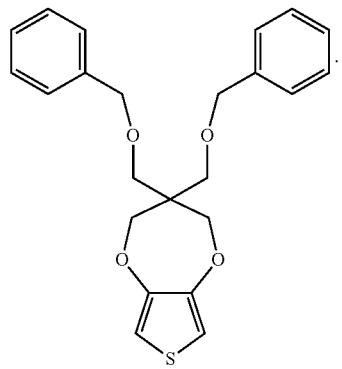

(II)

An embodiment of the present invention provides a method for preparing the blue thiophene electrochromic compound shown above, comprising:

step 1: allowing thiophene and bromine to undergo halogenation under a heating condition, to give tetrabromothiophene;

step 2: allowing tetrabromothiophene and zinc powder to undergo a reduction reaction in the presence of acetic acid, to give 3,4-dibromothiophene;

step 3: allowing 3,4-dibromothiophene and sodium methoxide to undergo etherification in the presence of a catalyst, to give 3,4-dimethoxythiophene;

step 4: allowing 3,4-dimethoxythiophene and dibromoneopentyl glycol to undergo trans-etherification in the presence of a catalyst, to give 3,4-(2,2-dibromomethyl)propylenedioxythiophene;

step 5: allowing 3,4-(2,2-dibromomethyl)propylenedioxythiophene to undergo etherification with benzenemethanol, phenylethanol, and phenylpropanol, respectively, in the presence of NaH under a heating condition, to give 3,4-(2,2-bis(2-oxo-3-phenylpropyl))propylenedioxythiophene, 3,4-(2,2-bis(2-oxo-3-phenylbutyl))propylenedioxythiophene, and 3,4-(2,2-bis(2-oxo-3-phenylamyl))propylenedioxythiophene.

Wherein, in step 1, the ratio of thiophene to bromine in mole is from 1:4 to 1:6, and preferably 1:5. The reaction solvent may be chloroform or dichloromethane, and preferably chloroform. The reaction temperature is from 60 to 80° C., and preferably 80° C. The reaction time is from 24 to 48 hours, and preferably 24 hours.

In step 2, the ratio of tetrabromothiophene to zinc powder in mole is from 1:5 to 1:8, and preferably 1:6. The reaction solvent is a mixed solution of acetic acid and water in which the volume ratio of acetic acid to water is 2:1-3:1, and preferably 3:1. The reaction is conducted at room temperature for from 12 to 24 hours, and preferably 12 hours.

In step 3, the ratio of 3,4-dibromothiophene to sodium methoxide in mole is from 1:3 to 1:5, and preferably 1:4. The catalyst is CuI in an amount of 10-25 mol % and preferably 25 mol % of 3,4-dibromothiophene. The reaction solvent is methanol. The reaction temperature is from 60 to 80° C., and preferably 80° C. The reaction time is from 48 to 72 hours, and preferably 72 hours.

In step 4, the ratio of 3,4-dimethoxythiophene to dibromoneopentyl glycol in mole is from 1:1.5 to 1:3, and preferably 1:2. The catalyst is p-toluenesulfonic acid in an amount of 10-15 mol % and preferably 15 mol % of 3,4-dimethoxythiophene. The reaction solvent is trichloromethane or toluene, and preferably toluene. The reaction temperature is from 100 to 130° C., and preferably 120° C. The reaction time is from 18 to 24 hours, and preferably 24 hours.

In step 5, the ratio of 3,4-(2,2-dibromomethyl)propylenedioxythiophene to benzenemethanol, phenylethanol, or phenylpropanol in mole is from 1:2 to 1:4, and the ratio of 3,4-(2,2-dibromomethyl)propylenedioxythiophene to NaH in mole is from 1:4 to 1:8. Preferably, the ratio of the thiophene derivative 3,4-(2,2-dibromomethyl)propylenedioxythiophene:benzenemethanol, phenylethanol or phenylpropanol:NaH in mole is 1:2-4:4-8, and preferably 1:4:6. The reaction solvent is anhydrous DMF. The reaction is conducted at a temperature of 90-95° C., and preferably 95° C. for 16-24 hrs, and preferably 24 hrs.

An embodiment of the present invention provides use of said blue thiophene electrochromic compound for preparing an electrochromic device.

An embodiment of the present invention further provides an assembly comprising said blue thiophene electrochromic compound.

BRIEF DESCRIPTION OF DRAWINGS

The exemplary embodiments will be described by way of examples with reference to the figures, in which.

DETAILED DESCRIPTION OF INVENTION

Figure 1:
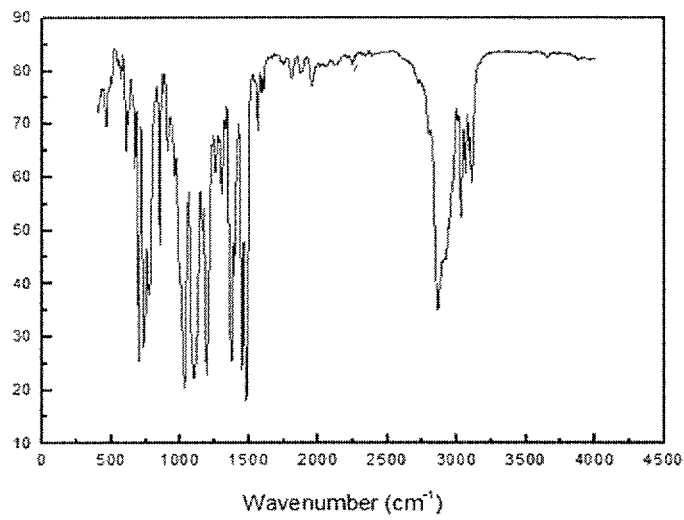
FIG. 1 shows Fourier transform infrared spectrum of a monomer prepared according to Example 1 of the present invention, wherein Y-axis represents the transmittance of infrared light, and X-axis represents wavelength.

The embodiments of the present invention will be described clearly and completely hereinafter. It is apparent that the described embodiments represent only a portion of rather than all of the embodiments of the present invention. Based on the embodiments of the present invention, persons of ordinary skill in the art can obtain other embodiments without creative work, all of which are encompassed within the present invention.

An embodiment of the present invention is directed to a blue thiophene electrochromic compound as shown by formula (I),

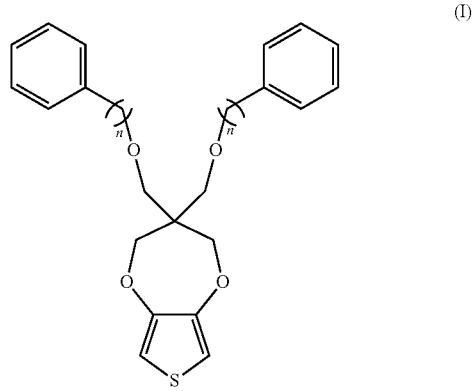

(I)

wherein, n is 1, 2, or 3.

Thus, said compound comprises 3,4-(2,2-bis(2-oxo-3-phenylpropyl))propylenedioxythiophene, 3,4-(2,2-bis(2-oxo-3-phenylbutyl))propylenedioxythiophene, 3,4-(2,2-bis (2-oxo-3-phenylamyl))propylenedioxythiophene.

For example, when n=1, said compound is 3,4-(2,2-bis (2-oxo-3-phenylpropyl))propylenedioxythiophene as shown by formula (II):

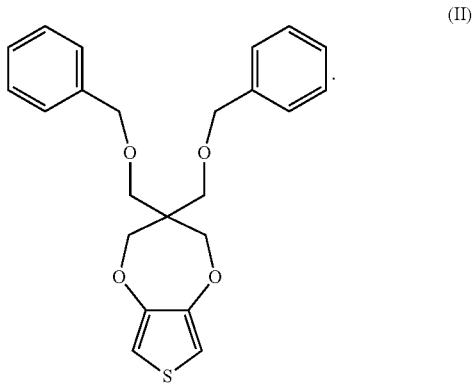 [SMILES: c1ccc(COCC2(COCc3ccccc3)COc3cscc3OC2)cc1]

(II)

Said compound has desired physical and chemical properties, can change color between blue and transparency, and has a cycle life greater than three thousand times. The compound can be useful for devices including electrochromic window, rearview mirror, electrochomeric display, and the like. The compound can be electropolymerized on the surface of the ITO glass to form a film. The resulting film has characteristics of low driving voltage (within ±1V), fast response time, and large transmittance difference between colored-state and bleached-state (up to 77.5%).

An embodiment of the present invention provides a method for preparing the blue thiophene electrochromic compound as shown above, comprising:

step 1: allowing thiophene and bromine to undergo halogenation under a heating condition, to give tetrabromothiophene;

step 2: allowing tetrabromothiophene and zinc powder to undergo a reduction reaction in the presence of acetic acid, to give 3,4-dibromothiophene;

step 3: allowing 3,4-dibromothiophene and sodium methoxide to undergo etherification in the presence of a catalyst, to give 3,4-dimethoxythiophene;

step 4: allowing 3,4-dimethoxythiophene and dibromoneopentyl glycol to undergo trans-etherification in the presence of a catalyst, to give 3,4-(2,2-dibromomethyl)propylenedioxythiophene;

step 5: allowing 3,4-(2,2-dibromomethyl)propylenedioxythiophene to undergo etherification with benzenemethanol, phenylethanol, and phenylpropanol, respectively, in the presence of NaH under a heating condition, to give 3,4-(2,2-bis(2-oxo-3-phenylpropyl))propylenedioxythiophene, 3,4-(2,2-bis(2-oxo-3-phenylbutyl))propylenedioxythiophene, and 3,4-(2,2-bis(2-oxo-3-phenylamyl))propylenedioxythiophene.

Here, in step 1, the ratio of thiophene to bromine in mole is from 1:4 to 1:6, and preferably 1:5. The reaction solvent may be chloroform or dichloromethane, and preferably chloroform. The reaction temperature is from 60 to 80° C., and preferably 80° C. The reaction time is from 24 to 48 hours, and preferably 24 hours. Under such conditions, the reaction in this step has advantages of saving starting materials and reducing reaction time on the premise of ensuring the synthetic yield.

In step 2, the ratio of tetrabromothiophene to zinc powder in mole is from 1:5 to 1:8, and preferably 1:6. The reaction solvent is a mixed solution of acetic acid and water in which the volume ratio of acetic acid to water is 2:1-3:1, and preferably 3:1. The reaction is conducted at room temperature for from 12 to 24 hours, and preferably 12 hours. Under such conditions, the reaction can achieve a maximum yield of 3,4-dibromothiophene.

In step 3, the ratio of 3,4-dibromothiophene to sodium methoxide in mole is from 1:3 to 1:5, and preferably 1:4. The catalyst is CuI in an amount of 10-25 mol % and preferably 25 mol % of 3,4-dibromothiophene. The reaction solvent is methanol. The reaction temperature is from 60 to 80° C., and preferably 80° C. The reaction time is from 48 to 72 hours, and preferably 72 hours. Under such conditions, the reaction is completely preformed with an enhanced yield.

In step 4, the ratio of 3,4-dimethoxythiophene to dibromoneopentyl glycol in mole is from 1:1.5 to 1:3, and preferably 1:2. The catalyst is p-toluenesulfonic acid in an amount of 10-15 mol % and preferably 15 mol % of 3,4-dimethoxythiophene. The reaction solvent is trichloromethane or toluene, and preferably toluene. The reaction temperature is from 100 to 130° C., and preferably 120° C. The reaction time is from 18 to 24 hours, and preferably 24 hours. Under such conditions, the reaction has advantages of saving starting materials and achieving a higher yield without increasing reaction time.

In step 5, the ratio of 3,4-(2,2-dibromomethyl)propylenedioxythiophene to benzenemethanol, phenylethanol, or phenylpropanol in mole is from 1:2 to 1:4, and the ratio of 3,4-(2,2-dibromomethyl)propylenedioxythiophene to NaH in mole is from 1:4 to 1:8. Preferably, the ratio of the thiophene derivative:alcohol:NaH in mole is 1:4:6. The reaction solvent is anhydrous DMF. The reaction is conducted at a temperature of 90-95° C., and preferably 95° C. for 16-24 hrs, and preferably 24 hrs. Under such conditions, the reaction can be completely preformed with an enhanced yield.

In one specific embodiment, the blue thiophene electrochromic compound (wherein n is 1) can be prepared according to the scheme below,

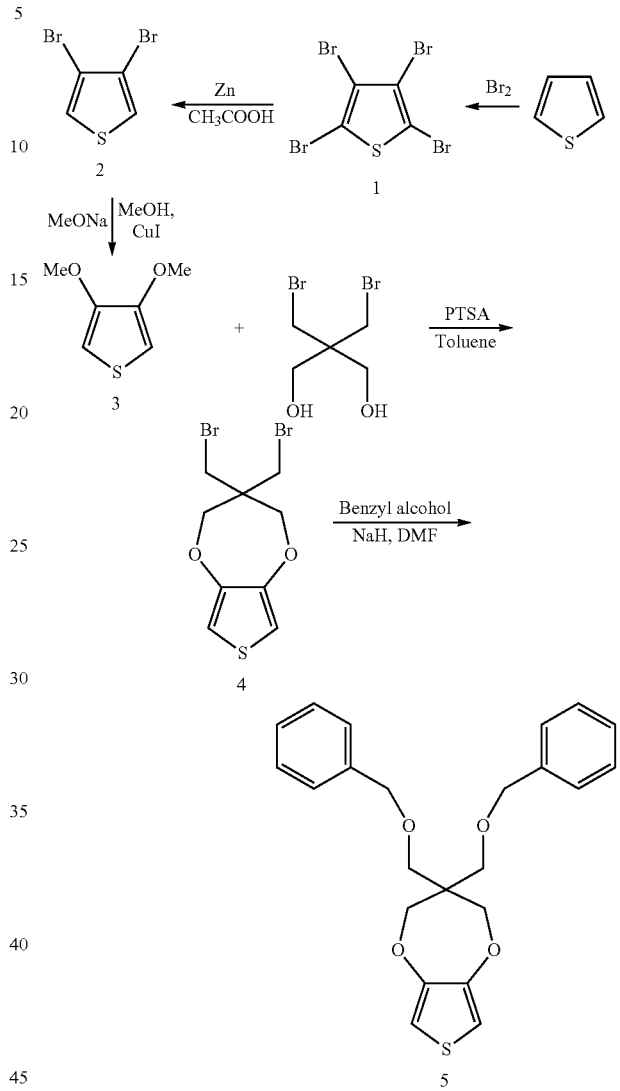

Step 1: Bromine (60 g, 375 mmol) is added dropwise a solution of tothiophene (6.3 g, 75 mmol) in chloroform (20 ml) with stirring, refluxing at 80° C. for 24 hrs. The mixture is poured into an appropriate amount of a NaOH solution and stirred to remove excess bromine. The reactant is washed with water several times, to give a while solid, tetrabromothiophene (compound 1), yield 80%.

Step 2: Tetrabromothiophene (20 g, 50 mmol) is added to a mixed solution of acetic acid (60 ml) and water (20 ml), to which zinc powder (19.6 g, 300 mmol) is added in portions. The mixture is stirred at room temperature for 12 hrs. Excess zinc powder is filleted out, and excess acetic and water are removed by rotary evaporation. The crude is passed through a chromatographic column, to give a colorless liquid, 3,4-dibromothiophene (compound 2), yield 73%.

Step 3: 3,4-dibromothiophene (10 g, 41.2 mmol) is added to 30 g of a methanol-sodium methoxide solution with a mass percent of 30% and stirred. Then CuI (1.96 g, 10.3 mmol) is added quickly, and refluxed at 80° C. for 72 hrs. The mixture is cooled to room temperature, to which a saturated NaCl solution is added. The mixture is extracted with ethyl acetate several times, and dried over anhydrous sodium sulfate to remove solvents. The crude is passed through a separation column, to give a oily liquid, 3,4-dimethoxythiophene (compound 3), yield 60%.

Step 4: 3,4-dimethoxythiophene (5 g, 34 mmol), dibromoneopentyl glycol (18 g, 68 mmol) p-toluenesulfonic acid (0.87 g, 5.1 mmol) and 400 ml of toluene are charged into a flask overhead linked to Soxhlet extractor, and react at 120° C. for 24 hrs. The reaction is cooled to room temperature, washed with water several times, dried over anhydrous sodium sulfate, and rotary-vaporized to remove solvent. The crude is passed through a separation column, to give a oily liquid, which upon condensation becomes a crystalline material, 3,4-(2,2-dibromomethyl)propylenedioxythiophene (compound 4), yield 75%.

Step 5: 50 ml DMF, NaH (0.28 g, 7 mmol), and benzenemethanol (0.5 g, 4.6 mmol) are charged into a flask and stirred with heating. Compound 4 (0.4 g, 1.16 mmol) is added to heated reactants and stirred with heating for 24 hrs. The mixture is cooled to room temperature, to which a saturated NaCl solution is added. The mixture is extracted with diethyl ether several times. The organic layer is washed with water and dried over anhydrous sodium sulfate. The solvents are removed by rotary evaporation. The crude is passed through a separation column, to give a colorless transparent oily liquid, the final product 3,4-(2,2-bis(2-oxo-3-phenylpropyl))propylenedioxythiophene (compound 5), yield 60%.

An embodiment of the present invention provides use of said blue thiophene electrochromic compound for preparing an electrochromic device. The electrochromic device includes, but is not limited to electrochromic window, rearview mirror, electrochomeric display.

An embodiment of the present invention further provides an assembly comprising said blue thiophene electrochromic compound (for example, 3,4-(2,2-bis(2-oxo-3-phenylpropyl))propylenedioxythiophene).

Said assembly according to the present invention is preferably an electrochromic film. The electrochromic film has advantages of low driving voltage, fast response time, transparent oxidation state and high transmittance. The polymer film formed by electroplating the polymer on the surface of the ITO glass has oxidizing potential and reducing potential within ±0.5V, for example, 0.1V and −0.25V, respectively, and response time for coloring and bleaching within 2 s, such as 1.7 s. The film has high transparent state, and the transmittance thereof can be up to 60%-80% in visible light region, such as 80%, and the transmittance difference reaches maximum of 60%-78% at 560 nm-600 nm. For example, the film has a maximum value of 77.5% at 580 nm.

The electrochromic film according to the embodiment of the present invention can be prepared by any film-forming method disclosed in the prior art. For example, said electrochromic film can be prepared as follows.

The compound 3,4-(2,2-bis(2-oxo-3-phenylpropyl))propylenedioxythiophene will be exemplified. 3,4-(2,2-bis(2-oxo-3-phenylpropyl))propylenedioxythiophene and lithium perchlorate are dissolved in propylene carbonate to achieve a concentration of 0.01M and 0.1M, respectively. The monomer is polymerized on the surface of an ITO glass via a cyclic voltammetry to form an electrochromic film, by using ITO glass as working electrode, platinum filament as counter electrode, and silver wire as reference electrode.

The embodiment of the present invention provides a novel blue electrochromic compound, the preparation thereof, and the use thereof. The compound can be polymerized on the surface of the ITO glass to form a film. The film has characteristics of low driving voltage (within ±1V), fast response time, and large transmittance difference between colored-state and bleached-state (up to 77.5%). The film can be used in the electrochromic window, rearview mirror, electrochomeric display, and the like.

The present invention will be described in details through specific examples below. These examples are only illustrative, and should not be interpreted as limiting the scope of the present disclosure.

EXAMPLE 1

The preparation procedures in this example are specifically shown below:

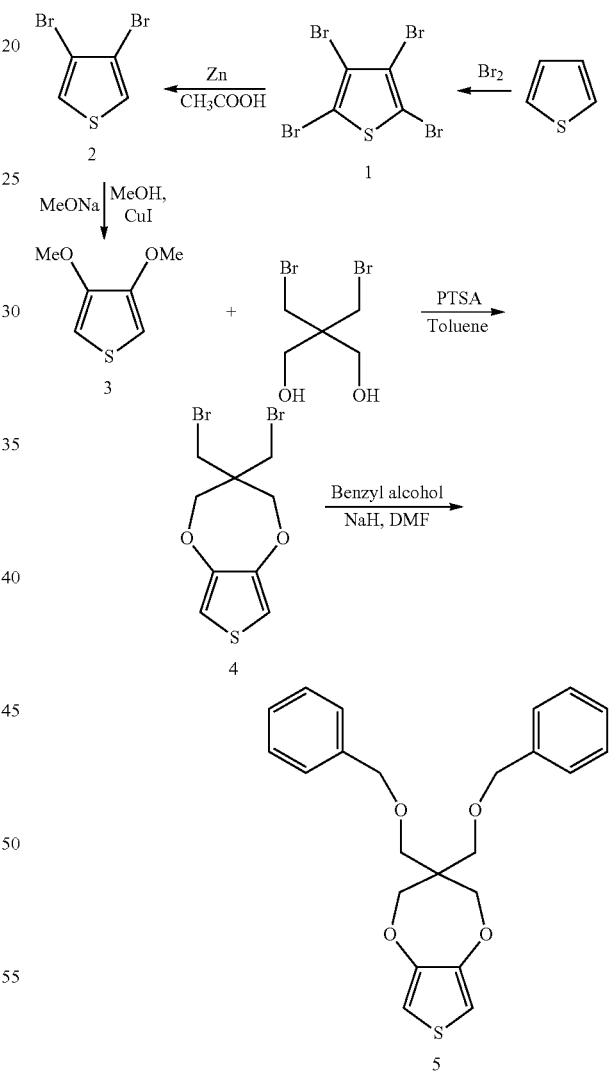

Step 1: Bromine (60 g, 375 mmol) is added dropwise a solution of tothiophene (6.3 g, 75 mmol) in chloroform (20 ml) with stirring, refluxing at 80° C. for 24 hrs. The mixture is poured into an appropriate amount of a NaOH solution and stirred to remove excess bromine. The reactant is washed with water several times, to give a while solid, tetrabromothiophene (compound 1), yield 80%, purity 95%.

Step 2: Tetrabromothiophene (20 g, 50 mmol) is added to a mixed solution of acetic acid (60 ml) and water (20 ml), to which zinc powder (19.6 g, 300 mmol) is added in portions. The mixture is stirred at room temperature for 12 hrs. Excess zinc powder is filleted out, and excess acetic and water are removed by rotary evaporation. The crude is passed through a chromatographic column, to give a colorless liquid, 3,4-dibromothiophene (compound 2), yield 73%, purity 95%.

Step 3: 3,4-dibromothiophene (10 g, 41.2 mmol) is added to 30 g of a methanol-sodium methoxide solution with a mass percent of 30% and stirred. Then CuI (1.96 g, 10.3 mmol) is added quickly, and refluxed at 80° C. for 72 hrs. The mixture is cooled to room temperature, to which a saturated NaCl solution is added. The mixture is extracted with ethyl acetate several times, and dried over anhydrous sodium sulfate to remove solvents. The crude is passed through a separation column, to give a oily liquid, 3,4-dimethoxythiophene (compound 3), yield 60%, purity 95%.

Step 4: 3,4-dimethoxythiophene (5 g, 34 mmol), dibromoneopentyl glycol (18 g, 68 mmol), p-toluenesulfonic acid (0.87 g, 5.1 mmol) and 400 ml of toluene are charged into a flask overhead linked to Soxhlet extractor and react at 120° C. for 24 hrs. The reaction is cooled to room temperature, washed with water several times, dried over anhydrous sodium sulfate, and rotary-vaporized to remove solvents. The crude is passed through a separation column, to give a oily liquid, which upon condensation becomes a crystalline material, 3,4-(2,2-dibromomethyl)propylenedioxythiophene (compound 4), yield 75%, purity 95%.

Step 5: 50 ml DMF, NaH (0.28 g, 7 mmol), and benzenemethanol (0.5 g, 4.6 mmol) are charged into a flask and stirred with heating. Compound 4 (0.4 g, 1.16 mmol) is added to heated reactants and stirred with heating for 24 hrs. The mixture is cooled to room temperature, to which a saturated NaCl solution is added. The mixture is extracted with diethyl ether several times. The organic layer is washed with water and dried over anhydrous sodium sulfate. The solvents are removed by rotary evaporation. The crude is passed through a separation column, to give a colorless transparent oily liquid, the final product 3,4-(2,2-bis(2-oxo-3-phenylpropyl))propylenedioxythiophene (compound 5), yield 60%, purity 95%.

The Fourier transform infrared spectrum of the monomer prepared in this example is shown in FIG. 1, in which x-axis represents wavelength, and y-axis represents transmittance. Here, peaks above 3000 nm are stretching vibration peaks of C—H bonds on the thiophene and benzene rings; peaks at 2700-3000 nm are stretching vibration peaks of saturated C—H bonds; peaks at 1400-1500 nm are backbone vibration peaks of the thiophene and benzene rings; peaks at 1000-1300 nm are stretching vibration peaks of C—O bonds; and peaks at 650-1000 nm are out-of-plane bending vibration peaks of C—H bonds.

Figure 2:
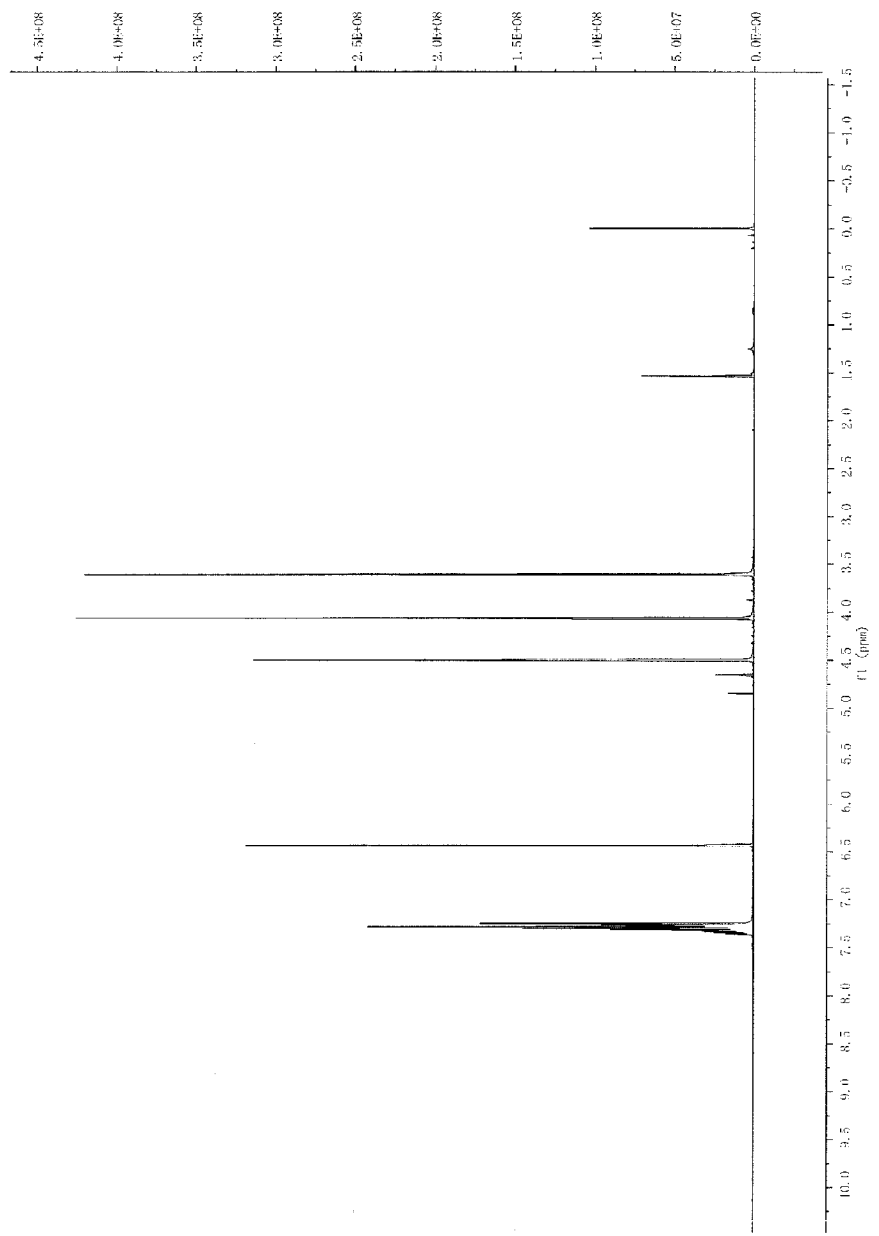
FIG. 2 shows $^1$HNMR of a monomer prepared according to Example 1 of the present invention, wherein Y-axis represents peak intensity, and X-axis represents chemical shift.

$^1$H-NMR of the monomer prepared in this example is shown in FIG. 2, in which y-axis represents peak intensity, and x-axis represents chemical shift. Peak at $\delta$=6.43 corresponds to the hydrogen atoms at 2,5-position of the thiophene ring; peak at $\delta$=4.06 corresponds to the hydrogen atoms at the 7-member ring linked to the thiophene ring; peak at $\delta$=3.60 corresponds to the hydrogen atoms of the methylene group linked to the 7-member ring; peak at $\delta$=4.5 corresponds to the hydrogen atoms of the methylene group linked to the benzene ring; peaks at $\delta$=7.25-7.35 correspond to the hydrogen atoms on the benzene ring.

Figure 3:
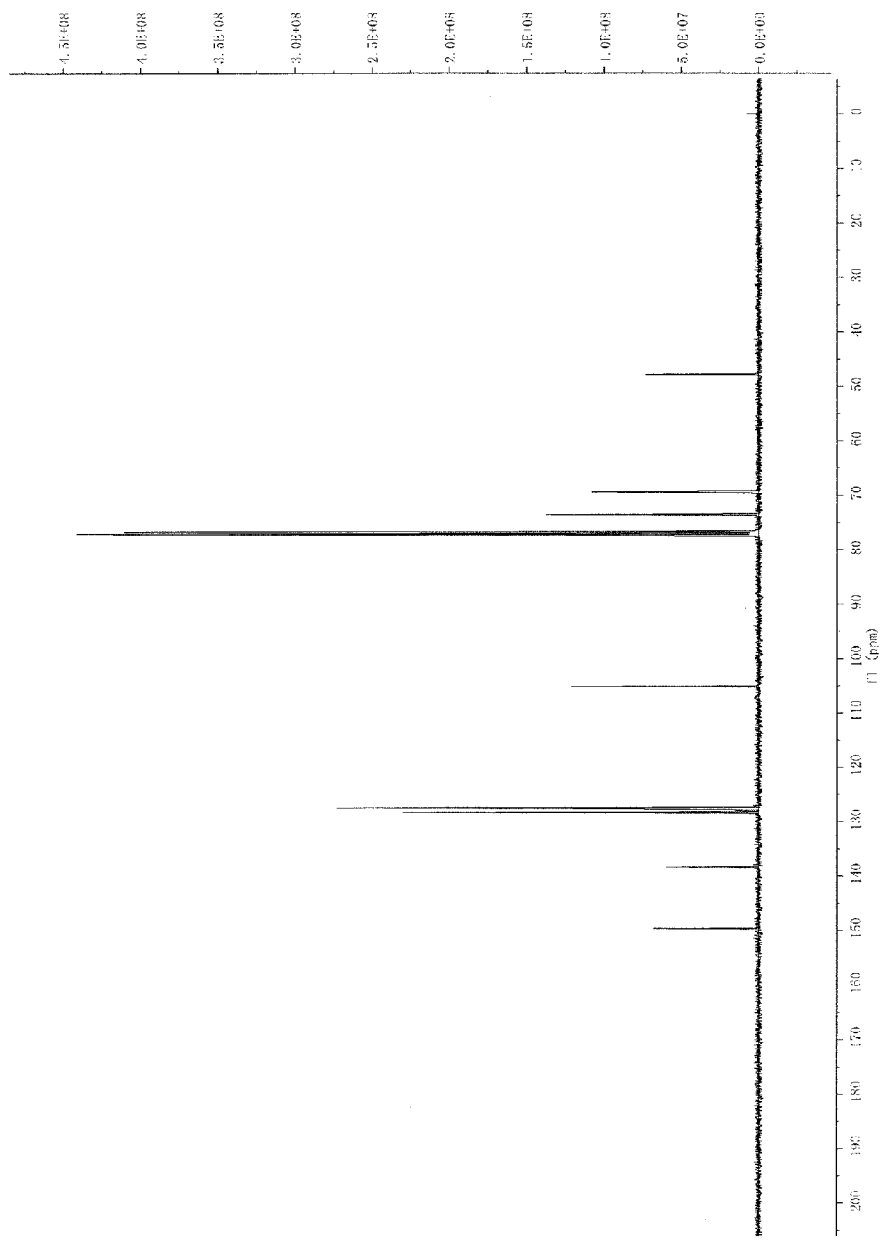
FIG. 3 shows $^{13}$CNMR of a monomer prepared according to Example 1 of the present invention, wherein Y-axis represents peak intensity, and X-axis represents chemical shift.

$^{13}$C-NMR of the monomer prepared in this example is shown in FIG. 3, in which y-axis represents peak intensity, and x-axis represents chemical shift. Peaks at $\delta$=105, 150 correspond to the carbon atoms on the thiophene ring; peaks at $\delta$=73.6, 47.8, 73.5 correspond to the carbon atoms of the methylene group and quaternary carbon atom on the 7-member ring, and carbon atoms of the methylene group linked to the 7-member ring, respectively; peak at $\delta$=69.5 corresponds to the carbon atom of the methylene group linked to the benzene ring; peaks at $\delta$=138, 128, 127.4, 127.5 corresponds to the carbon atoms on the benzene ring.

Figure 4:
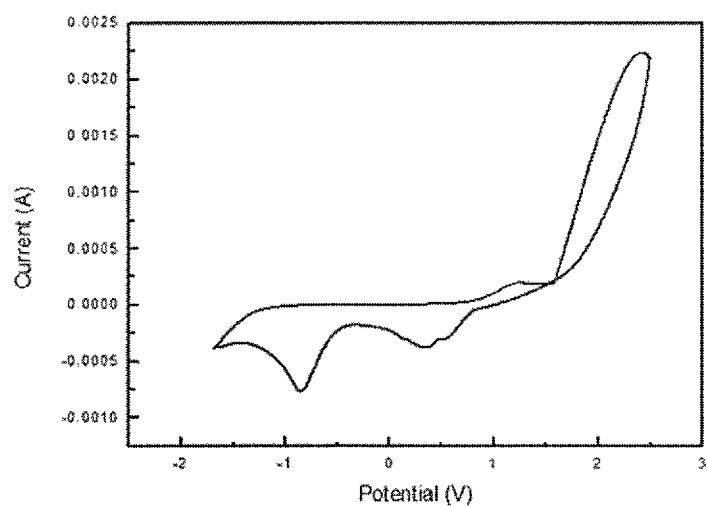
FIG. 4 shows cyclic voltammetry curves of a monomer prepared according to Example 1 of the present invention, wherein Y-axis represents the magnitude of electric current, and X-axis represents applied voltage.

Cyclic voltammetry curves of the monomer prepared in this example are shown in FIG. 4, wherein Y-axis represents the magnitude of electric current, and X-axis represents applied voltage. This figure shows that the polymerization voltage of the monomer is about 2.4V.

The polymer formed by the blue electrochromic compound produced in this example exhibits property parameters as follows. The polymer has oxidizing potential and reducing potential of 0.1V and −0.25V, respectively. Response times for both coloring and bleaching are 1.7 s. The film has high transparent state. The film has transmittance of up to 80% in visible light region. The transmittance difference reaches a maximum value of 77.5% at 580 nm. The yield of the final product (referring to the product of reaction yields in five steps) according to the scheme in this example is about 16% with a purity of 95%.

EXAMPLE 2

The procedure in Example 2 is the same as that in Example 1, except that phenethyl alcohol is used to replace benzenemethanol to conduct step 5. The final product is 3,4-(2,2-bis(2-oxo-3-phenylbutyl))propylenedioxythiophene. The yield in step 5 is 62% with a purity of 95%. The film formed by electropolymerizing the final product exhibits colored state of a light blue, has transmittance of 30% at 600 nm, and possesses a maximum transmittance difference of 50% in visible light range.

EXAMPLE 3

The procedure in Example 3 is the same as that in Example 1, except that phenylpropyl alcohol is used to replace benzenemethanol to conduct step 5. The final product is 3,4-(2,2-bis(2-oxo-3-phenylamyl))propylenedioxythiophene. The yield in step 5 is 60% with a purity of 95%. The film formed by electropolymerizing the final product exhibits colored state of a light blue, has transmittance of 45% at 600 nm, and possesses a maximum transmittance difference of 35% in visible light range.

EXAMPLE 4

As compared to Example 1, differences rely on:
In step 1, the ratio of thiophene to bromine in mole is 1:5. The reaction solvent is chloroform. The reaction temperature is 80° C. The reaction time is 24 hours. Yield: 80%; purity: 95%.

In step 2, the ratio of tetrabromothiophene to zinc powder in mole is 1:6. The reaction solvent is a mixed solution of acetic acid and water in which the volume ratio of acetic acid to water is 3:1. The reaction is conducted at room temperature for 12 hours. Yield: 73%; purity: 95%.

In step 3, the ratio of 3,4-dibromothiophene to sodium methoxide in mole is 1:4. The catalyst is CuI in an amount of 25 mol % of 3,4-dibromothiophene. The reaction solvent is methanol. The reaction temperature is 80° C. The reaction time is 72 hours. Yield: 60%; purity: 95%.

In step 4, the ratio of 3,4-dimethoxythiophene to dibromoneopentyl glycol in mole is 1:2. The catalyst is p-toluenesulfonic acid in an amount of 15 mol % of 3,4-dimethoxythiophene. The reaction solvent is toluene. The reaction temperature is 120° C. The reaction time is 24 hours. Yield: 75%; purity: 95%.

In step 5, the ratio of 3,4-(2,2-dibromomethyl)propylenedioxythiophene:benzenemethanol, phenylethanol or phenylpropanol:NaH in mole is 1:4:6. The reaction solvent is anhydrous DMF. The reaction is conducted at 95° C. for 24 hrs. Yield: 60%; purity: 95%.

The yield of the final product (referring to the product of reaction yields in five steps) in this example is about 16% with a purity of 95%.

EXAMPLE 5

As compared to Example 1, differences rely on:

In step 1, the ratio of thiophene to bromine in mole is 1:4. The reaction solvent is dichloromethane. The reaction temperature is 60° C. The reaction time is 24 hours. Yield: 70%; purity: 95%.

In step 2, the ratio of tetrabromothiophene to zinc powder in mole is 1:5. The reaction solvent is a mixed solution of acetic acid and water in which the volume ratio of acetic acid to water is 2:1. The reaction is conducted at room temperature for 12 hours. Yield: 67%; purity: 95%.

In step 3, the ratio of 3,4-dibromothiophene to sodium methoxide in mole is 1:3. The catalyst is CuI in an amount of 10 mol % of 3,4-dibromothiophene. The reaction solvent is methanol. The reaction temperature is 60° C. The reaction time is 48 hours. Yield: 45%; purity: 95%.

In step 4, the ratio of 3,4-dimethoxythiophene to dibromoneopentyl glycol in mole is 1:1.5. The catalyst is p-toluenesulfonic acid in an amount of 10 mol % of 3,4-dimethoxythiophene. The reaction solvent is trichloromethane. The reaction temperature is 100° C. The reaction time is 18 hours. Yield: 70%; purity: 95%.

In step 5, the ratio of 3,4-(2,2-dibromomethyl)propylenedioxythiophene:benzenemethanol, phenylethanol or phenylpropanol:NaH in mole is 1:2:4. The reaction solvent is anhydrous DMF. The reaction is conducted at 90° C. for 24 hrs. Yield: 56%; purity: 95%.

The yield of the final product (referring to the product of reaction yields in five steps) in this example is about 9% with a purity of 95%.

EXAMPLE 6

As compared to Example 1, differences rely on:

In step 1, the ratio of thiophene to bromine in mole is 1:6. The reaction solvent is chloroform. The reaction temperature is 70° C. The reaction time is 48 hours. Yield: 80%; purity: 95%.

In step 2, the ratio of tetrabromothiophene to zinc powder in mole is 1:8. The reaction solvent is a mixed solution of acetic acid and water in which the volume ratio of acetic acid to water is 3:1. The reaction is conducted at room temperature for 24 hours. Yield: 73%; purity: 95%.

In step 3, the ratio of 3,4-dibromothiophene to sodium methoxide in mole is 1:5. The catalyst is CuI in an amount of 20 mol % of 3,4-dibromothiophene. The reaction solvent is methanol. The reaction temperature is 70° C. The reaction time is 56 hours. Yield: 56%; purity: 95%.

In step 4, the ratio of 3,4-dimethoxythiophene to dibromoneopentyl glycol in mole is 1:3. The catalyst is p-toluenesulfonic acid in an amount of 12 mol % of 3,4-dimethoxythiophene. The reaction solvent is trichloromethane. The reaction temperature is 130° C. The reaction time is 20 hours. Yield: 75%; purity: 95%.

In step 5, the ratio of 3,4-(2,2-dibromomethyl)propylenedioxythiophene:benzenemethanol, phenylethanol or phenylpropanol:NaH in mole is 1:4:8. The reaction solvent is anhydrous DMF. The reaction is conducted at 95° C. for 20 hrs. Yield: 60%; purity: 95%.

The yield of the final product (referring to the product of reaction yields in five steps) in this example is about 16% with a purity of 95%.

EXAMPLE 7 BLUE ELECTROCHROMIC ASSEMBLY (ELECTROCHROMIC FILM) AND THE PREPARATION THEREOF

A solution of 3,4-(2,2-bis(2-oxo-3-phenylpropyl))propylenedioxythiophene prepared in Example 1 and lithium perchlorate in propylene carbonate is formulated, in which 3,4-(2,2-bis(2-oxo-3-phenylpropyl))propylenedioxythiophene is at concentration of 0.01M, and lithium perchlorate at concentration of 0.1M. The monomer is polymerized on the surface of an ITO glass via cyclic voltammetry to form an electrochromic film, by using ITO glass as working electrode, platinum filament as counter electrode, and silver wire as reference electrode.

The polymer formed by the blue electrochromic compound produced in this example exhibits property parameters as follows. The polymer has oxidizing potential and reducing potential of 0.1V and −0.25V, respectively. Response times for both coloring and bleaching are 1.7 s. The film has high transparent state. The film has transmittance of up to 80% in visible light region. The transmittance difference reaches a maximum value of 77.5% at 580 nm.

The electrochromic film can be prepared by common technical means disclosed in the prior art, and preferably by the method in this example.

Figure 5:
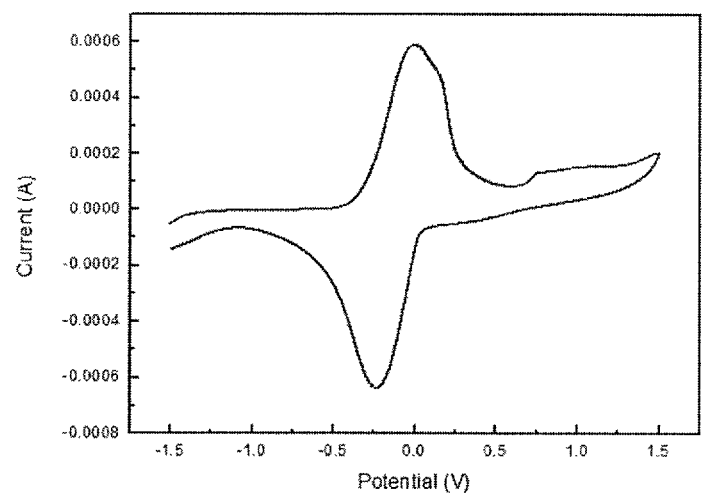
FIG. 5 shows cyclic voltammetry curves of a polymer film prepared according to Example 7 of the present invention, wherein Y-axis represents the magnitude of electric current, and X-axis represents applied voltage.

Cyclic voltammetry curves of the polymer film according to this example are shown in FIG. 5, wherein Y-axis represents the magnitude of electric current, and X-axis represents applied voltage. This figure shows that the oxidizing potential and reducing potential of the polymer are 0.1V and −0.25V, respectively.

Figure 6:
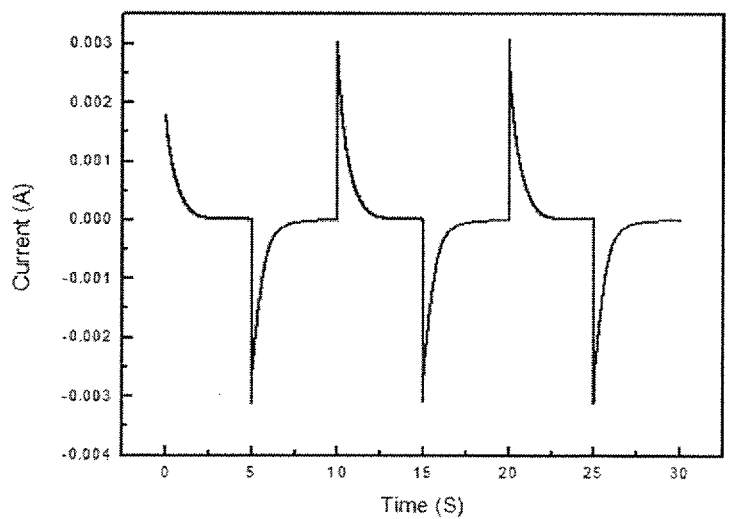
FIG. 6 shows a VSTEP curve of a polymer film prepared according to Example 7 of the present invention, wherein Y-axis represents the magnitude of electric current, and X-axis represents time.

A VSTEP curve of the polymer film of this example is shown in FIG. 6, wherein Y-axis represents the magnitude of electric current, and X-axis represents time. When response time is defined as 90% of the time required by the current changing from the maximum to zero, the film exhibits responses times for coloring and bleaching of 1.3 s and 1.4 s, respectively (if taking 95% of the time required by the current changing from the maximum to zero as response time, the response times for both coloring and bleaching are 1.7 s).

Figure 7:
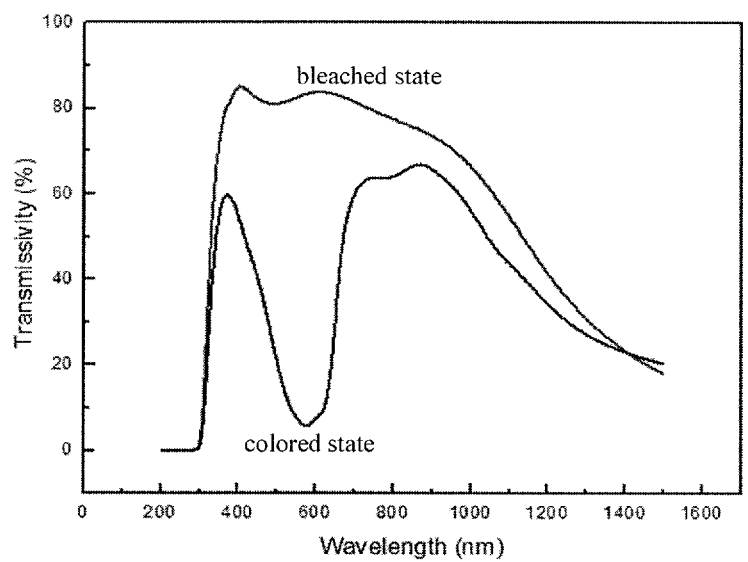
FIG. 7 is transmittance of colored state and bleached state of the polymer film prepared according to Example 7 of the present invention, wherein Y-axis represents transmittance, and X-axis represents wavelength.

A schematic illustration of transmittance of colored state and bleached state of the polymer film of this example is shown in FIG. 7, wherein Y-axis represents transmittance, and X-axis represents wavelength. In this figure, the upper curve represents transmittance of the polymer film in the bleached state, and the lower curve represents transmittance of the polymer film in the colored state. This figures shows that the film has transmittance of up to 80% at 400 nm and 600 nm in the bleached state, and the transmittance difference reaches a maximum value of 77.5% at 580 nm.

Figure 8:
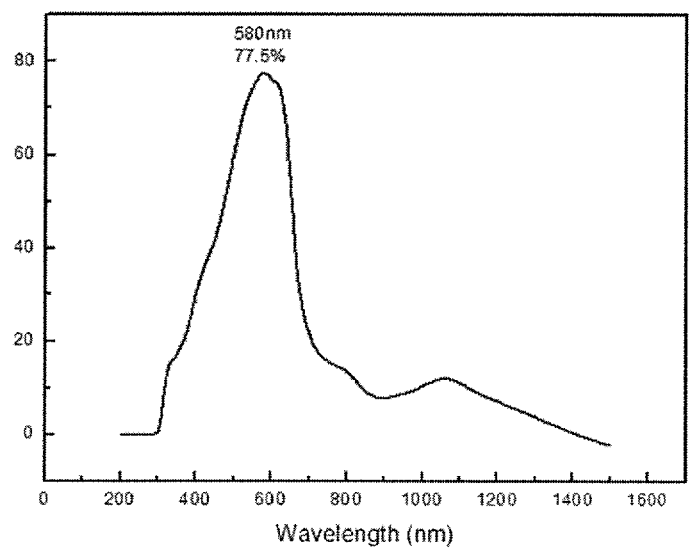
FIG. 8 is transmittance difference of colored state and bleached state of a polymer film prepared according to Example 7 of the present invention, wherein Y-axis represents transmittance of infrared light, X-axis represents wavelength, and the curve is generated by subtracting colored-state transmittance from bleached-state transmittance.

Transmittance difference of colored state and bleached state of the polymer film of this example is shown in FIG. 8, wherein Y-axis represents transmittance of infrared light, and X-axis represents wavelength. This curve is obtained by subtracting colored-state transmittance from bleached-state transmittance. This figure shows that the transmittance difference reaches a maximum value of 77.5% at 580 nm.

EXAMPLE 8 BLUE ELECTROCHROMIC ASSEMBLY (ELECTROCHROMIC FILM) AND THE PREPARATION THEREOF

A solution of 3,4-(2,2-bis(2-oxo-3-phenylbutyl))propylenedioxythiophene prepared in Example 1 and lithium perchlorate in propylene carbonate is formulated, in which 3,4-(2,2-bis(2-oxo-3-phenylbutyl))propylenedioxythiophene is at concentration of 0.01M, and lithium perchlorate at concentration of 0.1M. The monomer is polymerized on the surface of an ITO glass via a cyclic voltammetry to form an electrochromic film, by using ITO glass as working electrode, platinum filament as counter electrode, and silver wire as reference electrode.

The blue electrochromic material prepared in this example has high transparent state, of which the transmittance difference reaches a maximum value of 35% at 575 nm.

EXAMPLE 9 BLUE ELECTROCHROMIC ASSEMBLY (ELECTROCHROMIC FILM) AND THE PREPARATION THEREOF

A solution of 3,4-(2,2-bis(2-oxo-3-phenylamyl))propylenedioxythiophene prepared in Example 1 and lithium perchlorate in propylene carbonate is formulated, in which 3,4-(2,2-bis(2-oxo-3-phenylamyl))propylenedioxythiophene is at concentration of 0.01M, and lithium perchlorate at concentration of 0.1M. The monomer is polymerized on the surface of an ITO glass via a cyclic voltammetry to form an electrochromic film, by using ITO glass as working electrode, platinum filament as counter electrode, and silver wire as reference electrode.

The blue electrochromic material prepared in this example has high transparent state, of which the transmittance difference reaches a maximum value of 20% at 575 nm.

The embodiments described in the above examples can be further combined or replaced. And the examples only illustrate preferred examples of the present invention, and are not intended to limit the spirit and scope of the present invention. Without departing from the spirit of the present invention, person of ordinary skill in the art can make various modifications or variations with regard to the technical solutions of the present invention, which will fall into the scope the invention.

This application claims priority to Chinese Patent Application No. 201310695498.3 filed on Dec. 17, 2013, the disclosure of which is incorporated herein in its entirety as part of the present application.

The invention claimed is:

1. A method for preparing blue thiophene electrochromic compound as shown by formula (I),

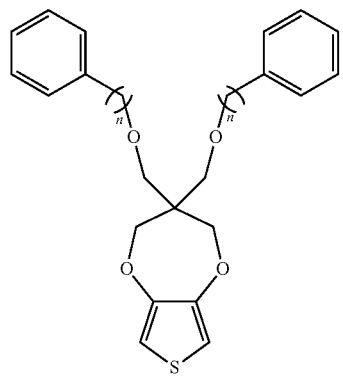

(I)

wherein, n is 1, 2, or 3, comprising:
step 1: halogenating thiophene and bromine with the ratio of thiophene to bromine in mole from 1:4 to 1:6 in the presence of a reaction solvent of chloroform or dichloromethane at a reaction temperature of 60 to 80° C. for 24 to 48 hours, to give tetrabromothiophene;
step 2: reducing tetrabromothiophene with zinc powder with the ratio of tetrabromothiophene to zinc powder in mole from 1:5 to 1:8 in the presence of a mixed solution of acetic acid and water in which the volume ratio of acetic acid to water is 2:1-3:1 at room temperature for from 12 to 24 hours, to give 3,4-dibromothiophene;
step 3: etherifying 3,4-dibromothiophene with sodium methoxide with the ratio of 3,4-dibromothiophene to sodium methoxide in mole from 1:3 to 1:5 in the presence of a catalyst CuI that is in an amount of 10-25 mol % of 3,4-dibromothiophene at a reaction temperature of 60 to 80° C. for 48 to 72 hours, to give 3,4-dimethoxythiophene;
step 4: trans-etherifying-3,4-dimethoxythiophene with dibromoneopentyl glycol with the ratio of 3,4-dimethoxythiophene to dibromoneopentyl glycol in mole from 1:1.5 to 1:3 in the presence of a catalyst p-toluenesulfonic acid that in an amount of 10-15 mol % of 3,4-dimethoxythiophenein a reaction solvent of trichloromethane or toluene at a reaction temperature of 100 to 130° C. for 18 to 24 hours, to give 3,4-(2,2-dibromomethyl)propylenedioxythiophene;
step 5: etherifying 3,4-(2,2-dibromomethyl)propylenedioxythiophene with benzenemethanol, phenylethanol, and phenylpropanol, respectively in the presence of NaH at a temperature of 90-95° C. for 16-24 hrs, to give 3,4-(2,2-bis(2-oxo-3-phenylpropyl))propylenedioxythiophene, 3,4-(2,2-bis(2-oxo-3-phenylbutyl))propylenedioxythiophene, and 3,4-(2,2-bis(2-oxo-3-phenylamyl))propylenedioxythiophene, wherein the ratio of 3,4-(2,2-dibromomethyl)propylenedioxythiophene to benzenemethanol, phenylethanol, or phenylpropanol in mole is from 1:2 to 1:4, the ratio of 3,4-(2,2-dibromomethyl)propylenedioxythiophene to NaH in mole is from 1:4 to 1:8.
2. The method of claim 1, wherein, in step 5, the ratio of 3,4-(2,2-dibromomethyl)propylenedioxythiophene:benzenemethanol, phenylethanol, or phenylpropanol:NaH in mole is 1:2-4:4-8.

* * * * *